US010059316B2

(12) United States Patent
Hanatsuka

(10) Patent No.: US 10,059,316 B2
(45) Date of Patent: Aug. 28, 2018

(54) ROAD SURFACE CONDITION ESTIMATING METHOD

(71) Applicant: BRIDGESTONE CORPORATION, Tokyo (JP)

(72) Inventor: Yasushi Hanatsuka, Tokyo (JP)

(73) Assignee: BRIDGESTONE CORPORATION, Chuo-ku, Tokyo (JP)

( * ) Notice: Subject to any disclaimer, the term of this patent is extended or adjusted under 35 U.S.C. 154(b) by 44 days.

(21) Appl. No.: 15/122,993

(22) PCT Filed: Jan. 5, 2015

(86) PCT No.: PCT/JP2015/050029
§ 371 (c)(1),
(2) Date: Sep. 1, 2016

(87) PCT Pub. No.: WO2015/133155
PCT Pub. Date: Sep. 11, 2015

(65) Prior Publication Data
US 2017/0072922 A1     Mar. 16, 2017

(30) Foreign Application Priority Data

Mar. 7, 2014    (JP) .................................. 2014-045591

(51) Int. Cl.
*B60C 19/00*       (2006.01)
*G01N 29/04*       (2006.01)
*B60T 8/172*       (2006.01)

(52) U.S. Cl.
CPC .............. *B60T 8/172* (2013.01); *B60C 19/00* (2013.01); *G01N 29/041* (2013.01);
(Continued)

(58) Field of Classification Search
CPC .. B60T 8/172; B60T 2210/12; B60T 2240/03;
B60T 2210/14; G01N 29/041;
(Continued)

(56) References Cited

U.S. PATENT DOCUMENTS

2002/0162389 A1* 11/2002 Yokota ..................... B60C 23/06
73/146
2008/0015763 A1* 1/2008 Kitazaki ............... B60C 23/064
701/70
(Continued)

FOREIGN PATENT DOCUMENTS

CN         102785646 A       11/2012
DE   10 2007 039 242 A1     2/2009
(Continued)

OTHER PUBLICATIONS

Communication dated Mar. 21, 2017 from the State Intellectual Property Office of the P.R.C. in counterpart Chinese application No. 2015800125122.
(Continued)

*Primary Examiner* — J M Saint Surin
(74) *Attorney, Agent, or Firm* — Sughrue Mion, PLLC

(57) ABSTRACT

A method is provided for estimating a road surface condition by accurately determining whether or not there has been any large input to a tire without increasing the number of sensors. An acceleration sensor is disposed on the tire to detect the vibration of the tire in motion. The positions of leading end point and trailing end point of tire contact patch are estimated from the peak positions appearing in the time-variable waveform of the vibration. At the same time, the contact time, extra-contact time, and revolution time of the tire are calculated from the estimated positions of leading end point and trailing end point. Then using one or more of the calculated data, it is determined whether or not the estimated positions of leading end point and trailing end
(Continued)

point are equal to the actual positions of leading end point and trailing end point. And if the result of the leading and trailing position determination is "incorrect estimation", the estimation of a road surface condition is not performed.

4 Claims, 5 Drawing Sheets

(52) U.S. Cl.
CPC ..... *B60C 2019/004* (2013.01); *B60T 2210/12* (2013.01); *B60T 2210/14* (2013.01); *B60T 2240/03* (2013.01); *G01N 2291/263* (2013.01)

(58) Field of Classification Search
CPC .............. G01N 2291/263; B60C 19/00; B60C 2019/004
USPC .......................................................... 73/584
See application file for complete search history.

(56) References Cited

U.S. PATENT DOCUMENTS

| | | | | |
|---|---|---|---|---|
| 2009/0105921 A1* | 4/2009 | Hanatsuka | ......... | B60G 17/0165 701/80 |
| 2010/0118989 A1* | 5/2010 | Sayana | ................. | H04L 5/0035 375/260 |
| 2011/0118989 A1* | 5/2011 | Morinaga | ............... | B60C 11/24 702/34 |
| 2012/0296493 A1 | 11/2012 | Wakao | | |
| 2013/0116972 A1* | 5/2013 | Hanatsuka | ............. | B60T 8/172 702/167 |
| 2014/0163770 A1* | 6/2014 | Wakao | ................ | B60W 40/068 701/1 |

FOREIGN PATENT DOCUMENTS

| | | | |
|---|---|---|---|
| EP | 0 818 683 A2 | | 1/1998 |
| EP | 2 301 769 A1 | | 3/2011 |
| EP | 2 573 594 A1 | | 3/2013 |
| JP | 2002-002472 A | | 1/2002 |
| JP | 2007055284 | * | 3/2007 |
| JP | 2007-106243 A | | 4/2007 |
| JP | 2008-302848 A | | 12/2008 |
| JP | 2011-203017 A | | 10/2011 |
| JP | 4817753 | * | 11/2011 |
| WO | 2013011992 A1 | | 1/2013 |

OTHER PUBLICATIONS

Communication dated Feb. 7, 2017 from the European Patent Office in counterpart Application No. 15759202.3.
Translation of International Preliminary Report on Patentability, dated Sep. 22, 2016, from the International Bureau in counterpart International application No. PCT/JP2015/050029.
Written Opinion of PCT/JP2015/050029 dated Mar. 31, 2015 [PCT/ISA/237].
International Search Report of PCT/JP2015/050029 dated Mar. 31, 2015 [PCT/ISA/210].

\* cited by examiner

ROAD SURFACE CONDITION ESTIMATING METHOD

CROSS REFERENCE TO RELATED APPLICATIONS

This application is a National Stage of International Application No. PCT/JP2015/050029, filed Jan. 5, 2015, claiming priority based on Japanese Patent Application No. 2014-045591, filed Mar. 7, 2014, the contents of all of which are incorporated herein by reference in their entirety.

BACKGROUND OF THE INVENTION

1. Field of the Invention

The present invention relates to a method for estimating a road surface condition under a traveling vehicle.

2. Description of the Related Art

To enhance the travel stability of a vehicle, it is desired that the road surface condition under a traveling vehicle is estimated with accuracy and the data thus obtained is fed back to vehicle control. If the road surface condition can be estimated in time, then it will be possible to operate such advanced control as ABS (antilock braking system) braking before taking any danger avoidance action such as braking, accelerating, or steering. With such facility, there will be a marked boost in the safety of vehicular operation.

In a proposed method for estimating a road surface condition (see Patent Document 1, for instance), a time-series waveform of vibration of the tire tread of a traveling vehicle is detected by an acceleration sensor installed on the inner liner of the tire. The time-series waveform is then subjected to a frequency analysis by extracting the time-series waveform of a domain including a leading end point of tire contact patch (footprint) and the time-series waveform of a domain including a trailing end point. From frequency spectrums thus derived, a band value $P_{fi}$ of the leading end domain and a band value $P_{kj}$ of the trailing end domain, which are the vibration levels of the plurality of frequency bands, are calculated respectively. And a road surface condition is estimated from these band values $P_{fi}$ and $P_{kj}$.

It should be noted that the positions of leading end point and trailing end point of tire footprint can be identified from the positions of peaks appearing in the time-series waveform of tire vibration. However, when the tire receives an excessive input (impact), such as when going over a bump or a curb, a conspicuous peak appears in the time-series waveform. In such cases, the positions of leading end point and trailing end point can sometimes be estimated incorrectly.

A solution to this problem as disclosed in Patent Document 1 is the installation of an acceleration sensor for monitoring on the suspension. And when the value of acceleration detected by the acceleration sensor for monitoring exceeds a predetermined threshold value, it is determined that there has been an excessive input (hereinafter referred to as large input) to the tire, and the estimation of a road surface condition is canceled.

RELATED ART DOCUMENT

Patent Document

Patent Document 1: Japanese Unexamined Patent Application Publication No. 2011-242303

SUMMARY OF THE INVENTION

Problem to be Solved by the Invention

However, the method disclosed in Patent Document 1 requires the installation of an acceleration sensor for monitoring on the suspension (unsprung).

The present invention has been made in view of the above-described problem, and an object of the invention is to provide a method for estimating a road surface condition by accurately determining whether or not there has been any large input to the tire, without an increase in the number of sensors.

Means for Solving the Problem

The present invention provides a method for estimating a road surface condition under a tire in motion from a time-series waveform of tire vibration detected by a vibration detecting means. The method includes estimating positions of a leading end point and a trailing endpoint of tire contact patch from peak positions appearing in the time-series waveform, calculating one or more of contact time, extra-contact time, and revolution time, which is the time for one revolution of the tire, from the estimated positions of leading end point and trailing end point, and determining whether or not the estimated positions of leading end point and trailing end point are equal to the actual positions of leading end point and trailing end point, based on one or more of the calculated contact time, extra-contact time, and revolution time. And the estimation of a road surface condition is not performed when it is determined that one or both of the positions of leading end point and trailing end point estimated in the above step of estimating are not equal to the actual positions of leading end point and trailing end point.

Here, the leading end point refers to the time, or the position on the tire circumference, at which the circumferential position of the tire where the vibration detecting means is installed (hereinafter referred to as measuring point) engages with the road surface, on the time-series waveform of tire vibration, and the trailing end point the time, or the position on the tire circumference, at which the measuring point disengages from the road surface.

By implementing the above-described arrangement, it is possible to avoid incorrect estimation of a large peak appearing in the time-series waveform of tire vibration when there has been a large input to the tire, as the peak at the leading end point or the peak at the trailing end point. Therefore the road surface condition can be estimated with accuracy.

It is to be understood that the foregoing summary of the invention does not necessarily recite all the features essential to the invention, and subcombinations of all these features are intended to be included in the invention.

BEST MODE FOR CARRYING OUT THE INVENTION

Figure 1:
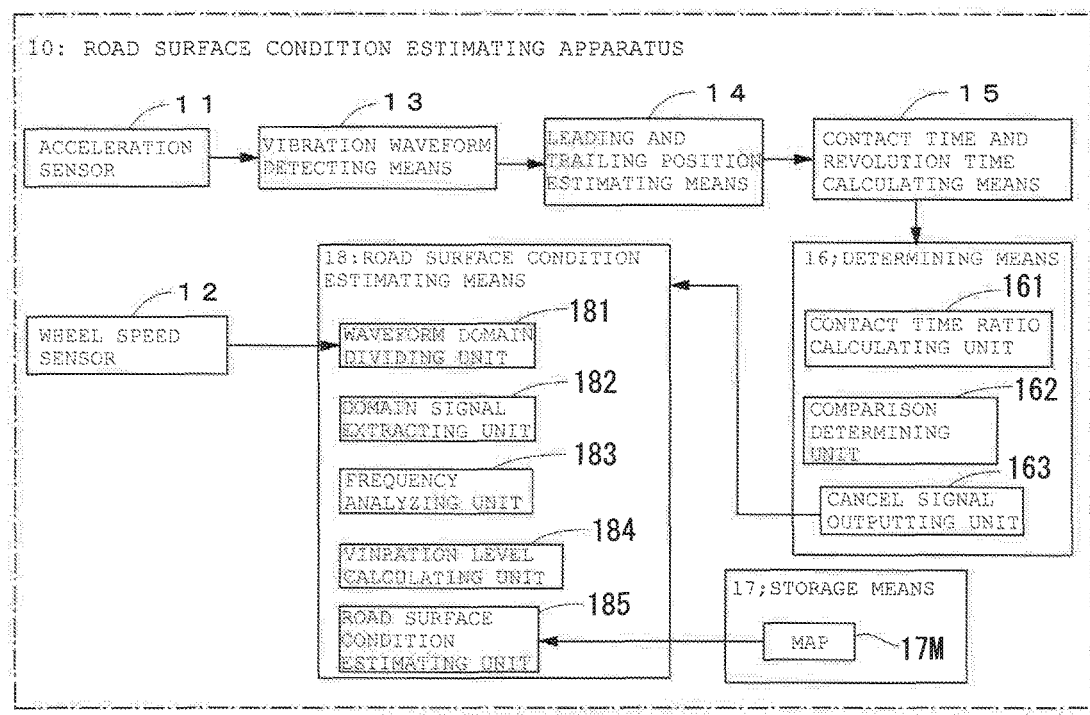
FIG. 1 is a diagram showing a configuration of a road surface condition estimating apparatus in accordance with the present invention.

FIG. 1 is a functional block diagram of a road surface condition estimating apparatus 10 according to an embodiment of the present invention.

The road surface condition estimating apparatus 10 includes an acceleration sensor 11 as a vibration detecting means, a wheel speed sensor 12 as a wheel speed detecting means, a vibration waveform detecting means 13, a leading and trailing position estimating means 14, a contact time and revolution time calculating means 15, a determining means 16, a storage means 17, and a road surface condition estimating means 18.

The respective means cited above, namely, the vibration waveform detecting means 13 to the determining means 16 and the road surface condition estimating means 18, may be constituted by computer software, for instance, and the storage means 17 by a RAM and ROM, and they are all incorporated into a vehicle control unit installed on a vehicle body.

Figure 2:
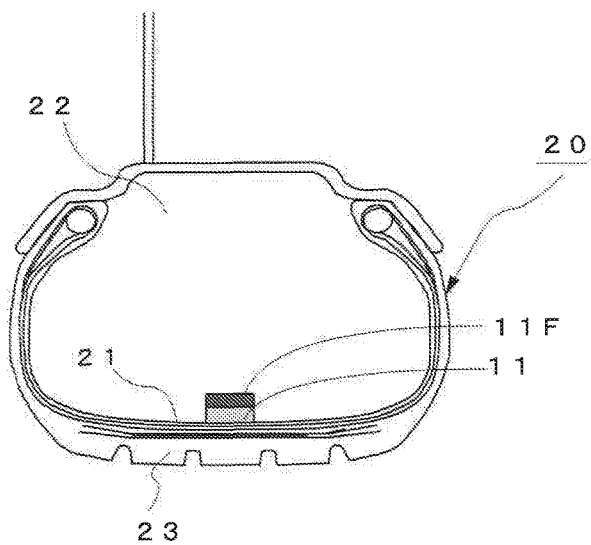
FIG. 2 is an illustration showing an example of disposition of an acceleration sensor.

The acceleration sensor 11, as shown in FIG. 2, is disposed nearly at the midportion of the inner liner 21 on the tire air chamber 22 side of the tire 20. And the acceleration sensor 11 detects the vibration inputted to the tread 23 of the tire 20 from the road surface as acceleration. In the present example, the acceleration sensor 11, which is so disposed that the detecting direction thereof is the tire circumferential direction, detects the circumferential vibration of the tire inputted from the road surface. Hereinafter, the position of the acceleration sensor 11 (to be exact, the position on the surface of the tread 23 radially outside of the acceleration sensor 11) is referred to as the measuring point. It is to be noted that the output of the acceleration sensor 11 is sent to a vehicle control unit installed on the vehicle body by a transmitter 11F, for instance.

The wheel speed sensor 12 detects the revolution speed of the wheel (hereinafter referred to as wheel speed). The wheel speed sensor 12 is comprised, for instance, of a rotor formed with gear teeth on its periphery and rotating together with the wheel, a yoke constituting a magnetic circuit in association with the rotor, and a coil for detecting changes in magnetic flux of the magnetic circuit. A wheel speed sensor of a known electromagnetic induction type or the like may be used for detecting the angle of rotation of the wheel.

The vibration waveform detecting means 13 detects a time-series waveform of vibration inputted to the tire 20 in motion, which is tire vibration on a time-series plot, outputted by the acceleration sensor 11.

Figure 3:
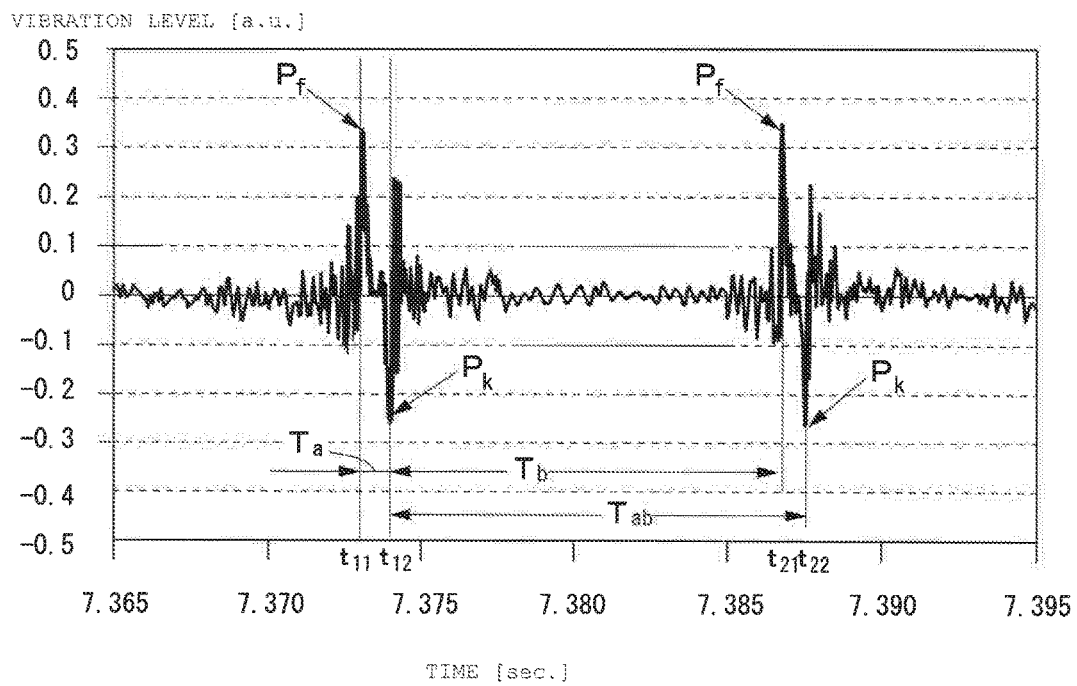
FIG. 3 is a diagram showing an example of a time-series waveform of vibration.

As shown in FIG. 3, there appear two conspicuous peaks, one positive and one negative, in every revolution of the tire in the time-series waveform of vibration.

The peak (a positive peak here) appearing first in the time-series waveform of vibration is the leading end point $P_f$, which is the peak occurring when the measuring point engages with the road surface. The peak (a negative peak here) appearing next is the trailing end point $P_k$, which is the peak occurring when the measuring point disengages from the road surface.

The leading and trailing position estimating means 14 detects two peaks appearing first, one positive and one negative, from the time-series waveform of vibration, thereby estimating the times of appearance of these peaks to be the position $t_{11}$ of the leading end point $P_f$ and the position $t_{12}$ of the trailing end point $P_k$, respectively. Also, the leading and trailing position estimating means 14 estimates the times of the two peaks, one positive and one negative, appearing next to be the position $t_{21}$ of the next leading end point $P_f$ and the position $t_{22}$ of the next trailing end point $P_k$, respectively.

The contact time and revolution time calculating means 15 calculates the contact time $T_a$, which is the space of time when the measuring point is in contact with the road surface, from the difference between the position $t_{11}$ of the leading end point $P_f$ and the position $t_{12}$ of the trailing endpoint $P_k$. At the same time, the contact time and revolution time calculating means 15 calculates the revolution time $T_{ab}$, which is the time taken by one revolution of the tire 20, from the difference between the position $t_{12}$ of the first trailing end point $P_k$ and the position $t_{22}$ of the next trailing end point $P_k$. Note that the difference between the position $t_{12}$ of the trailing end point $P_k$ and the position $t_{21}$ of the next leading endpoint $P_f$ is the extra-contact time $T_b$.

Accordingly, $T_a=t_{12}-t_{11}$, $T_b=t_{21}-t_{12}$, $T_{ab}=t_{22}-t_{12}$

Also, the revolution time $T_{ab}$ may be calculated from the difference between the position $t_{11}$ of the leading end point $P_f$ and the position $t_{21}$ of the next leading end point $P_f$.

The determining means 16 includes a contact time ratio calculating unit 161, a comparison determining unit 162, and a cancel signal outputting unit 163.

The contact time ratio calculating unit 161 calculates the contact time ratio R, which is the ratio between the contact time $T_a$ and revolution time $T_{ab}$ calculated by thecontact time and revolution time calculating means 15.

The comparison determining unit 162 determines whether or not the position $t_{11}$ of the leading end point $P_f$ and the positions $t_{12}$ and $t_{22}$ of the trailing end point $P_k$ estimated by the leading and trailing position estimating means 14 are all equal to the actual positions of leading end point and trailing end point.

More specifically, it is determined whether or not the contact time ratio R is in the predetermined contact time ratio range [from R1 to R2]. When the contact time ratio R is in the contact time ratio range (R1≤R≤R2), it is determined that $t_{11}$, $t_{12}$, and $t_{22}$ estimated by the leading and trailing position estimating means 14 are all equal to the actual positions of leading end point and trailing end point (normal positions).

On the other hand, when the contact time ratio R is not in the contact time ratio range (R<R1 or R>R2), it is determined that one, two, or all of the estimated position $t_{11}$ of the leading end point $P_f$ and positions $t_{12}$ and $t_{22}$ of the trailing end point $P_k$ are not equal to the actual positions of leading end point and trailing end point (incorrect estimation).

The cancel signal outputting unit 163 outputs a cancel signal, which is a command signal to cancel the operation of road surface estimation, to the road surface condition estimating means 18 when the comparison determining unit 162 has determined that the estimation was incorrect, that is, there was a failure in estimating the position of the leading end point $P_f$ and the position of the trailing end point $P_k$ correctly.

The storage means 17 stores a map 17M showing a relationship between predetermined road surface conditions and calculated values of vibration level.

The road surface condition estimating means 18 includes a waveform domain dividing unit 181, a domain signal extracting unit 182, a frequency analyzing unit 183, a vibration level calculating unit 184, and a road surface condition estimating unit 185. The road surface condition estimating means 18 estimates a road surface condition only when it is determined that the positions of leading end point and trailing end point estimated by the leading and trailing position estimating means 14 are equal to the actual positions of leading end point and trailing end point. And it cancels the estimation of a road surface condition when a cancel signal is outputted from the cancel signal outputting unit 163.

Figure 4:
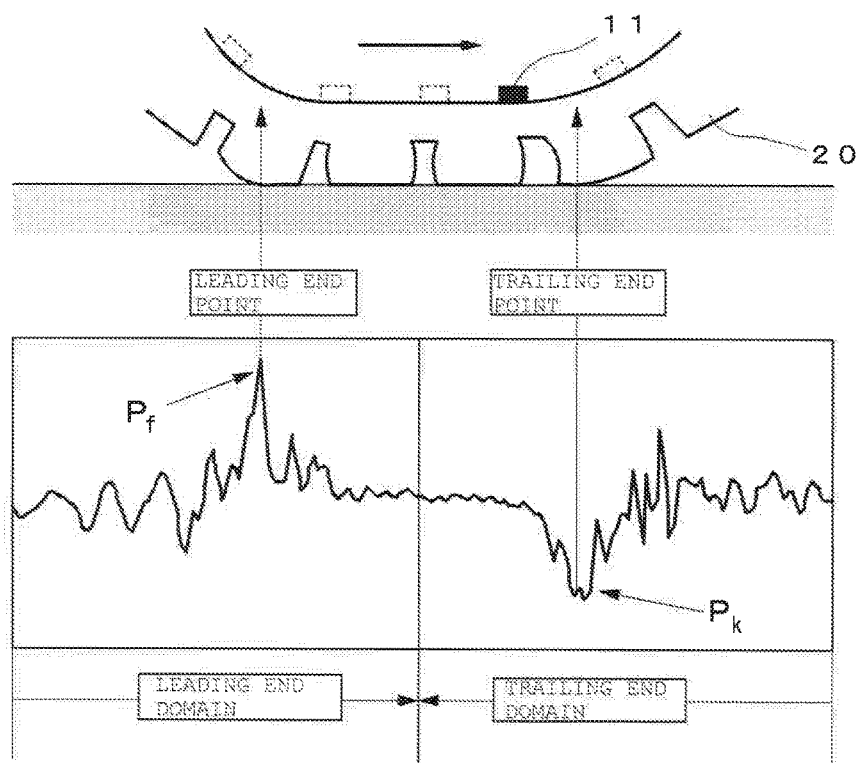
FIG. 4 is a diagram showing a leading end pint and a trailing end point.

The waveform domain dividing unit 181 extracts a vibration waveform for a single revolution of the tire, using the position of the leading end point $P_f$ or the trailing end point $P_k$ estimated by the leading and trailing position estimating means 14 and the revolution speed of the tire 20 detected by the wheel speed sensor 12. At the same time, it divides the vibration waveform into the data of two domains, namely, the leading end domain and the trailing end domain as shown in FIG. 4.

The domain signal extracting unit 182 extracts the time-series waveforms of vibration level in the respective domains.

The frequency analyzing unit 183, which is constituted by a frequency analyzing means such as an FFT analyzer, generates frequency spectrums by performing a frequency analysis on the extracted time-series waveforms of vibration level, respectively.

The vibration level calculating unit 184 calculates the leading end vibration level $V_f$, which is the vibration level in a predetermined frequency band of the frequency spectrum in the leading end domain, and the trailing end vibration level $V_k$, which is the vibration level in a predetermined frequency band of the frequency spectrum in the trailing end domain. At the same time, it calculates a calculated value S of the vibration levels, using these vibration levels. The calculated value S may be the ratio of the leading end vibration level $V_f$ to the trailing end vibration level $V_k$, for instance.

The road surface condition estimating unit 185 estimates the condition of the road surface under the traveling vehicle, based on the map 17M, stored in the storage means 17, showing the relationship between the predetermined road surface conditions and the calculated value S of the vibration levels and the data of the calculated value S of the vibration levels calculated by the vibration level calculating unit 184.

Figure 5:
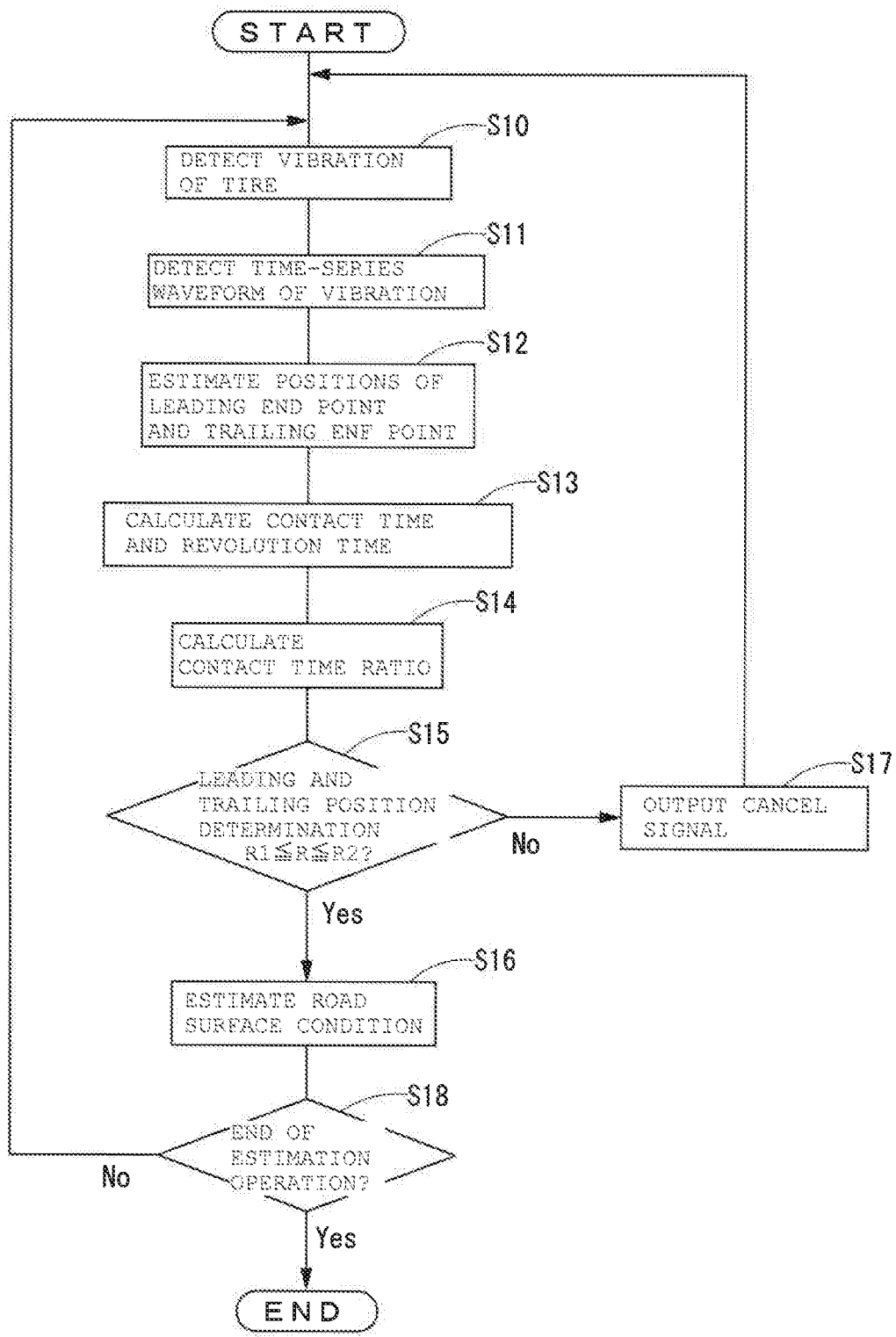
FIG. 5 is a flowchart showing a method for estimating a road surface condition according to an embodiment.

Now, a description is given of a method for estimating a road surface condition according to this embodiment, with reference to the flowchart of FIG. 5.

Firstly, the circumferential vibration of the tire 20 in motion is detected by the acceleration sensor 11 (step S10). And the output is sent to the vibration waveform detecting means 13, where the time-series waveform of vibration, which is the vibration waveform in the tire circumferential direction on a time-series plot, is determined (step S11).

Next, from the time-series waveform of vibration as shown in FIG. 3, the position $t_{11}$ of the leading end point $P_f$ appearing first, the position $t_{12}$ of the trailing end point $P_k$ appearing first, and the position $t_{22}$ of the trailing end point $P_k$ appearing next are estimated by the leading and trailing position estimating means 14 (step S12).

Then, using the $t_{11}$, $t_{12}$, and $t_{22}$ detected in the step S12, the contact time $T_a$ and the revolution time $T_{ab}$ are calculated by the contact time and revolution time calculating means 15 (step S13).

Next, after the contact time ratio R, which is the ratio between the contact time $T_a$ and the revolution time $T_{ab}$, is calculated (step S14), it is determined by the determining means 16 whether or not the contact time ratio R is in the predetermined contact time ratio range [from R1 to R2]. At the same time, a leading and trailing position determination is performed, in which it is determined whether or not the $t_{11}$, $t_{12}$, and $t_{22}$ detected in step S12 are all equal to the actual positions of the leading end point $P_f$ and trailing end point $P_k$ (step S15).

Figure 6:
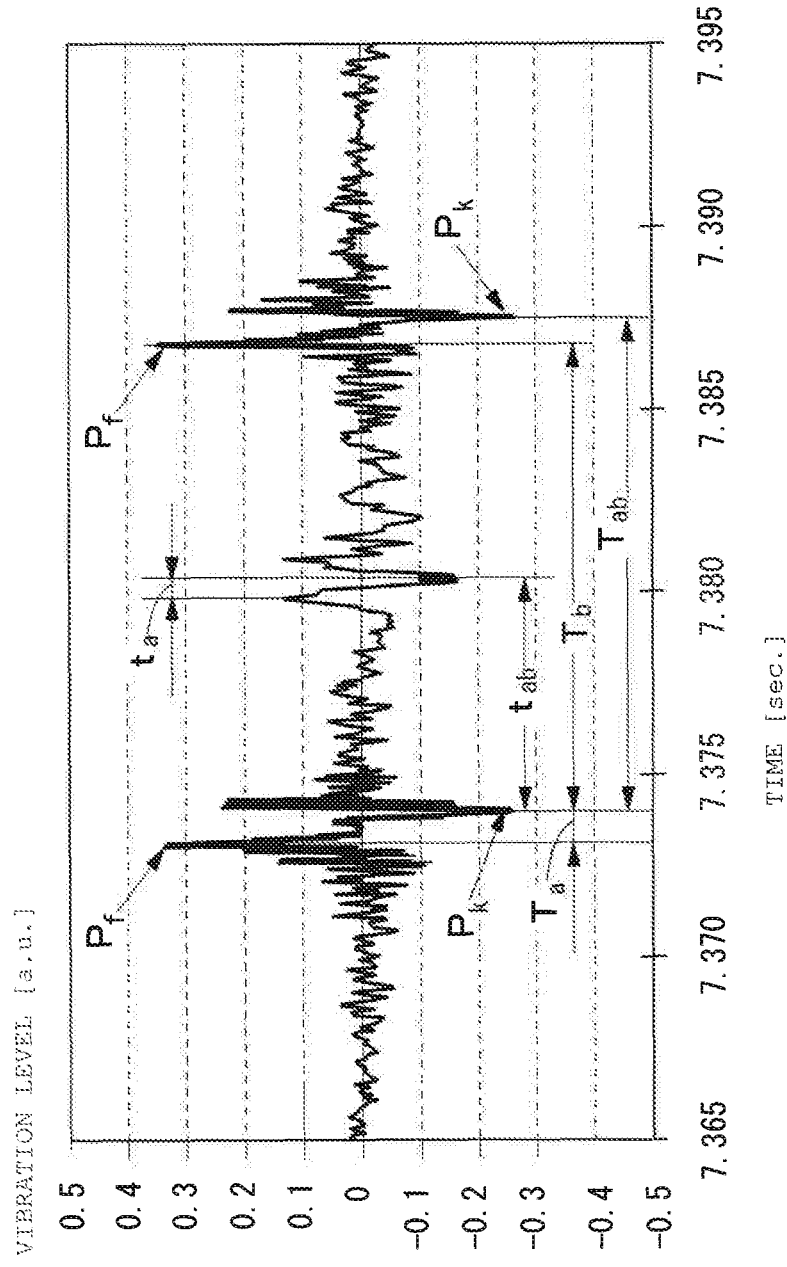
FIG. 6 is a diagram showing an example of a time-series waveform of vibration when there has been a large input to the tire.

It is to be noted that when the tire receives an excessive input (hereinafter referred to as large input), such as when going over a bump or a curb, a conspicuous peak appears in the time-series waveform as shown in FIG. 6. In such cases, the positions of leading end point $P_f$ and trailing end point $P_k$ can sometimes be estimated incorrectly.

For example, if the position of a large input as shown in the figure is estimated to be the position of the trailing end point $P_k$ occurring next, then the revolution time $T_{ab}$ calculated will be shorter than the actual revolution time $T_{ab}$.

Also, if the position of the large input is estimated to be the position of the leading end point $P_f$ occurring next, then the contact time $t_a$ will be shorter than the actual contact time $T_a$.

Hence, a range of contact time ratio [from R1 to R2] is predetermined for the contact time ratio R, and the R is compared against the lower limit value R1 and the upper limit value R2 of the contact time ratio range. Then by determining whether or not the contact time ratio R is in the predetermined contact time ratio range, a leading and trailing position determination can be performed, in which it is determined whether or not the position $t_{11}$ of the leading end point $P_f$ and the positions $t_{12}$ and $t_{22}$ of the trailing end point $P_k$ estimated by the leading and trailing position estimating means 14 are equal to the actual positions of leading end point and trailing end point.

When the result of leading and trailing position determination in step S15 is "normal positions", the procedure goes to step S16, where an estimation of a road surface condition is performed using the time-series waveform of vibration level.

On the other hand, when the result of leading and trailing position determination is "incorrect estimation", a cancel signal is outputted to the road surface condition estimating means 18 (step S17), and the procedure goes back to step S10, where the detection of the circumferential vibration of the tire 20 in motion is continued.

When a cancel signal is outputted, the estimation of a road surface condition is canceled.

Note that at the end of step S16, it is determined whether the operation of estimating a road surface condition has been completed (step S18). And if the operation of estimation is to be continued, the procedure returns to step S10, where the detection of the circumferential vibration of the tire 20 in motion is continued. If it is not to be continued, this operation is brought to an end.

The method for estimating a road surface condition in step S16 is as described below:

Firstly, a vibration waveform for one tire revolution is extracted from the time-series waveform of vibration inputted to the tire 20, which is outputted by the acceleration sensor 11. The extracted vibration waveform is divided into data of two domains, namely, the leading end domain and the trailing end domain. And then the time-series waveforms of vibration level in the two domains are extracted, respectively.

Next, the extracted time-series waveforms of vibration level are subjected to a frequency analysis, respectively. And from the frequency spectrums of the two domains resulting from the frequency analysis, the vibration levels $V_f$ and $V_k$ in predetermined frequency bands are calculated. Then a calculated value S is computed from the vibration levels $V_f$ and $V_k$.

Then the condition of the road surface under the traveling vehicle is estimated from the calculated value S and the map 17M showing the relationship between the predetermined road surface conditions and the calculated value $S_f$ of vibration levels.

More specifically, the vibration level $V_f$ in the frequency band of 8 to 10 kHz is calculated from the frequency spectrum of the leading end domain, and the vibration level $V_k$ in the frequency band of 1 to 3 kHz is calculated from the frequency spectrum of the trailing end domain. And the road surface condition is estimated by determining to which of the calculated value $S_f$ of the road surface the calculated value $S=V_f/V_k$ is closer.

According to the present embodiment, therefore, an acceleration sensor 11 is disposed on the tire 20 to detect the circumferential vibration of the tire 20 in motion. The positions of the leading end point $P_f$ and trailing end point $P_k$ of tire contact patch are estimated from the peak positions appearing in the time-variable waveform of the vibration. At the same time, the contact time $T_a$, extra-contact time $T_b$, and revolution time $T_{ab}$ of the tire 20 are calculated from the estimated positions of the leading end point $P_f$ and trailing end point $P_k$. Then using one or more of the calculated data, a leading and trailing position determination is performed, in which it is determined whether or not the estimated positions of the leading end point $P_f$ and trailing endpoint $P_k$ are equal to the actual positions of leading end point and trailing end point. And if the result of determination is "incorrect estimation", the estimation of a road surface condition is not performed. Accordingly, it is possible to accurately determine whether or not there has been any excessive input to the tire without an increase in the number of sensors. Thus, the accuracy in the estimation of a road surface condition can be improved.

In step S15, the arrangement may also be such that when the contact time or the contact length estimated from the contact time is outside the predetermined range of contact length, it is determined that one or both of the estimated positions of leading end point and trailing end point are not equal to the actual positions of leading end point and trailing end point.

Also, in step S15, the arrangement may be such that when the revolution time or the revolution length estimated from the revolution time is outside the predetermined range of revolution length, it is determined that one or both of the estimated positions of leading end point and trailing end point are not equal to the actual positions of leading end point and trailing end point.

This makes it possible to determine whether or not the positions of leading end point and trailing end point estimated using a simple method are equal to the actual positions of leading end point and trailing end point.

Also, in step S15, the arrangement may be such that the contact time ratio, which is the ratio between the contact time and the revolution time, is calculated and when the calculated contact time ratio is outside the predetermined range of contact time ratio, it is determined that one or both of the estimated positions of leading end point and trailing end point are not equal to the actual positions of leading end point and trailing end point.

As a result, it is possible to determine, without using the wheel speed, whether or not the estimated positions of leading endpoint and trailing endpoint are equal to the actual positions of leading end point and trailing end point. This can further improve the accuracy of the estimation of a road surface condition.

EXPERIMENTAL EXAMPLE

Figure 7:
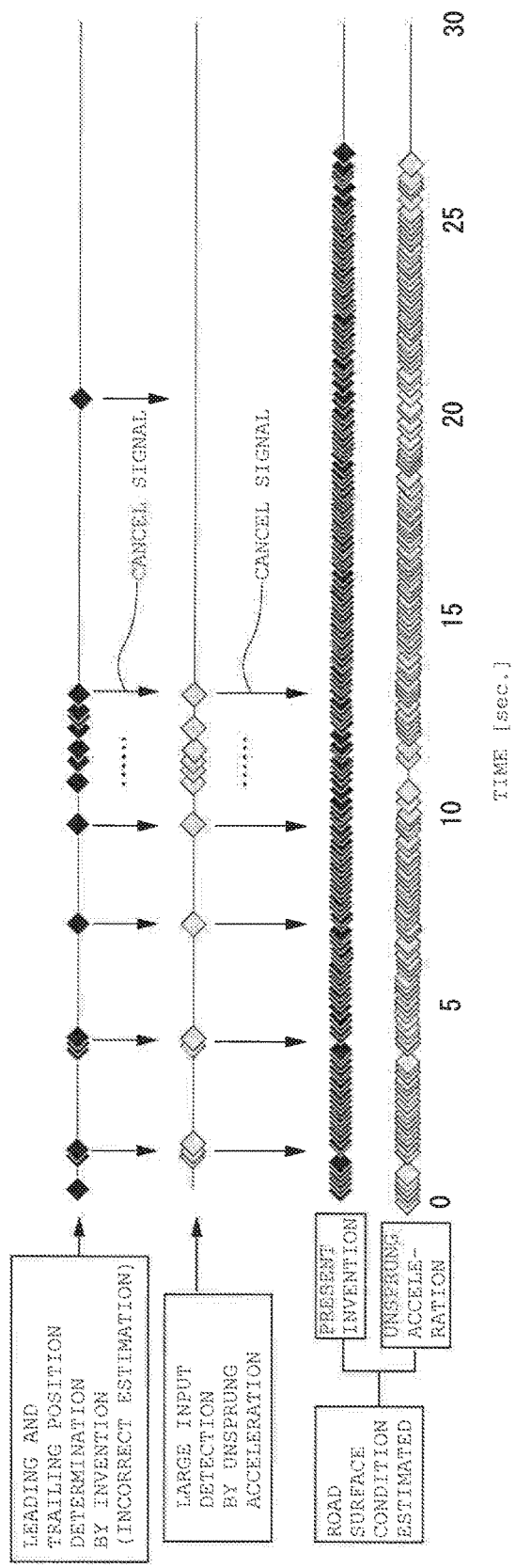
FIG. 7 is a diagram for explaining the accuracy of estimation of a large input in accordance with the present invention.

FIG. 7 is a diagram comparing the results of incorrect estimation as determined by the leading and trailing position determination of the present invention with the results of large input detection by the monitoring acceleration sensor as described in the afore-mentioned Patent Document 1. As is clear from the diagram, the leading and trailing position determination of the present invention displays a determination accuracy equal to or better than that of the large input detection described in Patent Document 1.

Thus, it has been confirmed that even when there is a large input, the invention provides the determination with accuracy whether or not the positions of leading end point and trailing end point estimated from the vibration waveform are equal to the actual positions of leading end point and trailing end point.

Thus far, the invention has been described with reference to specific embodiments thereof and an experimental example. However, the technical scope of this invention is not to be considered as limited to those embodiments. It will be evident to those skilled in the art that various modifications and changes may be made thereto without departing from the broader spirit and scope of the invention. It will also be evident from the scope of the appended claims that all such modifications are intended to be included within the technical scope of this invention.

For example, in the foregoing embodiment, an acceleration sensor 11 is disposed on the tire air chamber 21 side of the inner liner 21 of the tire 20 to detect the circumferential vibration of the tire. However, the arrangement may be such that the acceleration sensor is attached on the knuckle to detect the fore-aft vibration of the tire.

Also, in the foregoing embodiment, the positions of the leading end point $P_f$ and trailing end point $P_k$ and a road surface condition are estimated using the circumferential vibration of the tire detected by the acceleration sensor 11. However, the axial acceleration or radial acceleration of the tire may be used instead. Yet, when the radial acceleration of the tire is to be used, it is preferable that a differential acceleration derived by differentiating the detected radial acceleration of the tire is used, which will enable a more accurate estimation of the positions of the leading end point $P_f$ and trailing end point $P_k$.

Also, in the foregoing embodiment, a road surface condition under a traveling vehicle is estimated based on a calculated value S of the leading-end vibration level $V_f$ and traiing-end vibration level $V_k$ derived from the time-series waveform of tire vibration detected by the acceleration sensor 11 and the map 17M showing the relationship between the predetermined road surface conditions and the calculated value $S_f$. But this is not a limitation of the present invention. For example, the invention is applicable to an apparatus for estimating a road surface condition using a time-variable waveform of vibration of the tire in motion detected by a vibration detecting means as disclosed in Patent Document 1.

Also, in the foregoing embodiment, the vibration waveform is divided into the leading end domain and the trailing end domain, using the output of the wheel speed sensor 12. However, the vibration waveform may be divided into the leading end domain and the trailing end domain by converting the time-series waveform of the vibration waveform into the vibration waveforms at predetermined positions of the tire from the motional radius and the revolution time of the tire. Then the wheel speed sensor 12 may be omitted.

Accordingly, the present invention may be applicable to a road surface condition estimating apparatus having no wheel speed sensor 12 as a constituent element.

Also, in the foregoing embodiment, the leading and trailing position determination is performed using the contact time ratio R. However, the leading and trailing position determination may be performed using any one of the contact time, the extra-contact time, and the revolution time.

Also, the contact length and the revolution length may be used in the place of the contact time and the revolution time. Then there will be no dependence on the wheel speed. This will further improve the accuracy of leading and trailing position determination.

For example, when the contact time or the contact length is used, it is determined to be "incorrect estimation" when the contact time or the contact length is outside the predetermined range of contact length. Also, when the revolution time or the revolution length is used, it is determined to be "incorrect estimation" when the revolution time or the revolution length is outside the predetermined range of revolution length.

It should be noted that in the foregoing embodiment, it is determined whether or not one or both of the positions of leading end point and trailing end point estimated from the contact time $T_a$ and the revolution time $T_{ab}$ are equal to the actual positions of leading end point and trailing end point. However, since the extra-contact time $T_b$ is the difference between the revolution time $T_{ab}$ and the contact time $T_a$, it goes without saying that it can be determined whether or not one or both of the positions of leading end point and trailing end point estimated from the contact time $T_a$ and the extra-contact time $T_b$ or from the extra-contact time $T_b$ and the revolution time $T_{ab}$ are equal to the actual positions of leading end point and trailing end point.

DESCRIPTION OF REFERENCE NUMERALS

10 road surface condition estimating apparatus
11 acceleration sensor
12 wheel speed sensor
13 vibration waveform detecting means
14 leading and trailing position estimating means
15 contact time and revolution time calculating means
16 determining means
161 contact time ratio calculating unit
162 comparison determining unit
163 cancel signal outputting unit
17 storage means
18 road surface condition estimating means
181 waveform domain dividing unit
182 domain signal extracting unit
183 frequency analyzing unit
184 vibration level calculating unit
185 road surface condition estimating unit
20 tire
21 inner liner
22 tire air chamber
23 tread

The invention claimed is:

1. A method for estimating a road surface condition under a tire in motion from a time-series waveform of tire vibration detected by a vibration detector, the method comprising:
   estimating positions of a leading end point and a trailing end point of a tire contact area based on peak positions appearing in the time-series waveform;
   calculating one or more of a contact time, a non-contact time, and a revolution time, wherein the revolution time is a time corresponding to one revolution of the tire from the estimated positions of the leading end point and the trailing end point; and
   determining whether or not the estimated positions of the leading end point and the trailing end point are equal to actual positions of the leading end point and the trailing end point, based on one or more of the calculated contact time, the calculated non-contact time, and the calculated revolution time,
   wherein the estimation of a road surface condition is not performed after determining that one or both of the positions of the leading end point and the trailing end point estimated in the above step of estimating are not equal to the actual positions of the leading end point and the trailing end point.

2. The method for estimating a road surface condition according to claim 1, wherein, the step of determining that one or both of the positions of the leading end point and the trailing end point estimated in the above step of estimating are not equal to the actual positions of the leading end point and the trailing end point further comprises:
   determining that the contact time, or a contact length estimated from the contact time, is outside a predetermined range for the contact time or the contact length.

3. The method for estimating a road surface condition according to claim 1, wherein, the step of determining that one or both of the positions of the leading end point and the trailing end point estimated in the above step of estimating are not equal to the actual positions of the leading end point and the trailing end point further comprises:
   determining that the revolution time, or a revolution length estimated from the revolution time, is outside a predetermined range for the revolution time or the revolution length.

4. The method for estimating a road surface condition according to claim 1, wherein, the step of determining that one or both of the positions of the leading end point and the trailing end point estimated in the above step of estimating are not equal to the actual positions of the leading end point and the trailing end point further comprises:
   determining that a contact time ratio, which is a ratio of the contact time to the revolution time is outside a predetermined range for the contact time ratio.

* * * * *